United States Patent
Zdeblick et al.

[19]

[11] Patent Number: 5,984,967
[45] Date of Patent: *Nov. 16, 1999

[54] OSTEOGENIC FUSION DEVICES

[75] Inventors: Thomas Zdeblick, Madison, Wis.; William F. McKay, Memphis, Tenn.

[73] Assignee: SDGI Holdings, Inc., Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/603,674

[22] Filed: Feb. 19, 1996

Related U.S. Application Data

[63] Continuation-in-part of application No. 08/413,353, Mar. 30, 1995, Pat. No. 5,669,909, which is a continuation-in-part of application No. 08/411,017, Mar. 27, 1995, Pat. No. 5,782,919, and a continuation-in-part of application No. 08/482,038, Jun. 7, 1995, Pat. No. 5,645,084.

[51] Int. Cl.$^6$ ....................................................... A61F 2/44
[52] U.S. Cl. .............................................................. 623/17
[58] Field of Search ................................. 623/17, 18, 16; 606/60, 61, 69, 72

[56] References Cited

U.S. PATENT DOCUMENTS

| | | | |
|---|---|---|---|
| Re. 34,037 | 8/1992 | Inoue et al. | 604/93 |
| 3,486,505 | 12/1969 | Morrison | 128/303 |
| 3,848,601 | 11/1974 | Ma et al. | 128/305 |
| 4,309,777 | 1/1982 | Patil | 128/92 |
| 4,349,921 | 9/1982 | Kuntz | 3/1 |
| 4,501,269 | 2/1985 | Bagby | 128/92 |
| 4,526,909 | 7/1985 | Urist | 523/115 |
| 4,545,374 | 10/1985 | Jacobson | 128/303 |
| 4,596,574 | 6/1986 | Urist | 623/16 |
| 4,599,086 | 7/1986 | Doty | 623/17 |
| 4,627,853 | 12/1986 | Campbell et al. | 623/16 |
| 4,678,470 | 7/1987 | Nashef et al. | 623/16 |
| 4,743,256 | 5/1988 | Brantigan | 623/17 |
| 4,743,259 | 5/1988 | Bolander et al. | 623/16 |
| 4,759,766 | 7/1988 | Buettner-Janz et al. | 623/17 |
| 4,772,287 | 9/1988 | Ray et al. | 623/17 |
| 4,834,757 | 5/1989 | Brantigan | 623/17 |
| 4,863,476 | 9/1989 | Shepperd | 623/17 |
| 4,877,020 | 10/1989 | Vich | 128/92 |
| 4,878,915 | 11/1989 | Barantigan | 623/17 |
| 4,888,366 | 12/1989 | Chu et al. | 623/16 |
| 4,892,545 | 1/1990 | Day et al. | 623/17 |
| 4,904,261 | 2/1990 | Dove et al. | 623/17 |
| 4,917,704 | 4/1990 | Frey et al. | 623/17 |

(List continued on next page.)

FOREIGN PATENT DOCUMENTS

| | | |
|---|---|---|
| 0 077 159 | 10/1981 | European Pat. Off. . |
| 35 05 567 A1 | 8/1986 | Germany . |
| 40629667 | 10/1994 | Japan ........................ 623/11 |
| WO 91/06261 | 5/1991 | WIPO . |
| WO 94/11040 | 5/1994 | WIPO . |
| WO 95/15133 | 6/1995 | WIPO . |
| WO 96/22747 | 8/1996 | WIPO . |

*Primary Examiner*—David J. Isabella
*Attorney, Agent, or Firm*—Woodard, Emhardt, Naughton Moriarty & McNett

[57] ABSTRACT

An interbody fusion device in one embodiment includes a tapered body defining a hollow interior for receiving bone graft or bone substitute material. The body defines exterior threads which are interrupted over portions of the outer surface of the device. The fusion device includes truncated side walls so that on end view the body takes on a cylindrical form. The side walls are provided with vascularization openings, and the body wall device includes opposite bone ingrowth slots extending through the interrupted thread portion of the body. In another embodiment, the tapered body is solid and formed of a porous biocompatible material having sufficient structural integrity to maintain the intradiscal space and normal curvature. The material is preferably a porous tantalum having fully interconnected pores to facilitate complete bone tissue ingrowth into the implant. In further embodiments, the fusion devices are provided with osteogenic material to facilitate bone ingrowth. The osteogenic material can include bone morphogenic proteins in a suitable carrier determined by the configuration of the fusion device.

10 Claims, 11 Drawing Sheets

U.S. PATENT DOCUMENTS

| | | | |
|---|---|---|---|
| 4,932,975 | 6/1990 | Main et al. | 623/17 |
| 4,936,848 | 6/1990 | Bagby | 623/17 |
| 4,961,740 | 10/1990 | Ray et al. | 606/61 |
| 5,002,576 | 3/1991 | Fuhrmann et al. | 623/17 |
| 5,015,247 | 5/1991 | Michelson | 606/61 |
| 5,030,474 | 7/1991 | Saita et al. | 427/2 |
| 5,062,850 | 11/1991 | MacMillan et al. | 623/17 |
| 5,068,122 | 11/1991 | Kokubo et al. | 427/2 |
| 5,071,437 | 12/1991 | Steffee | 623/17 |
| 5,128,169 | 7/1992 | Saita et al. | 427/2 |
| 5,133,755 | 7/1992 | Brekke | 623/16 |
| 5,147,402 | 9/1992 | Bohler et al. | 623/16 |
| 5,147,404 | 9/1992 | Downey | 623/17 |
| 5,164,187 | 11/1992 | Constantz et al. | 424/423 |
| 5,188,670 | 2/1993 | Constntz | 118/667 |
| 5,192,327 | 3/1993 | Brantigan | 623/17 |
| 5,207,710 | 5/1993 | Chu | 623/16 |
| 5,236,456 | 8/1993 | O'Leary | 623/16 |
| 5,236,460 | 8/1993 | Barber | 623/17 |
| 5,258,029 | 11/1993 | Chu et al. | 623/16 |
| 5,279,831 | 1/1994 | Constantz et al. | 424/423 |
| 5,282,861 | 2/1994 | Kaplan | 623/16 |
| 5,290,312 | 3/1994 | Kojimoto et al. | 623/17 |
| 5,306,307 | 4/1994 | Senter et al. | 623/17 |
| 5,306,309 | 4/1994 | Wagner et al. | 623/17 |
| 5,306,310 | 4/1994 | Siebels | 623/17 |
| 5,330,826 | 7/1994 | Taylor et al. | 428/216 |
| 5,338,433 | 8/1994 | Maybee et al. | 205/178 |
| 5,344,654 | 9/1994 | Rueger et al. | 424/423 |
| 5,348,026 | 9/1994 | Davidson | 128/898 |
| 5,360,430 | 11/1994 | Lin | 606/61 |
| 5,366,508 | 11/1994 | Brekke | 623/16 |
| 5,371,191 | 12/1994 | Poser et al. | 530/350 |
| 5,397,364 | 3/1995 | Kozak et al. | 623/17 |
| 5,405,391 | 4/1995 | Hednerson et al. | 623/17 |
| 5,417,975 | 5/1995 | Lussi et al. | 424/423 |
| 5,425,769 | 6/1995 | Snyders, Jr. | 623/16 |
| 5,439,684 | 8/1995 | Prewett et al. | 424/422 |
| 5,443,515 | 8/1995 | Cohen et al. | 623/17 |
| 5,455,231 | 10/1995 | Constantz et al. | 514/21 |
| 5,458,638 | 10/1995 | Kuslich et al. | 623/17 |
| 5,464,439 | 11/1995 | Gendler | 623/16 |
| 5,507,813 | 4/1996 | Dowd et al. | 623/16 |
| 5,510,396 | 4/1996 | Prewett et al. | 523/113 |
| 5,514,180 | 5/1996 | Heggeness et al. | 606/60 |
| 5,585,116 | 12/1996 | Boniface et al. | 424/549 |
| 5,593,409 | 1/1997 | Michelson | 606/61 |
| 5,609,636 | 3/1997 | Kohrs et al. | 623/17 |
| 5,645,591 | 7/1997 | Kuberasampath | 623/16 |
| 5,646,084 | 7/1997 | McKay | 606/76 |
| 5,766,252 | 6/1998 | Henry et al. | 623/17 |
| 5,766,253 | 6/1998 | Brosnahan, III | 623/17 |

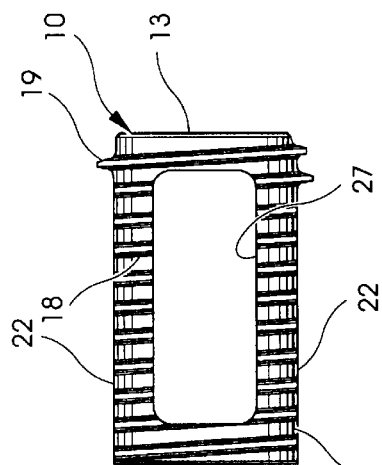
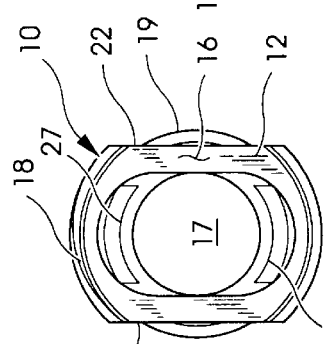
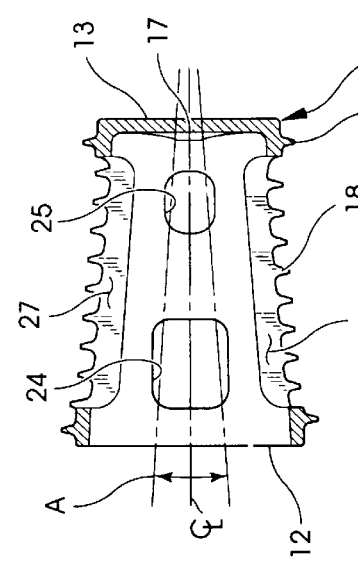
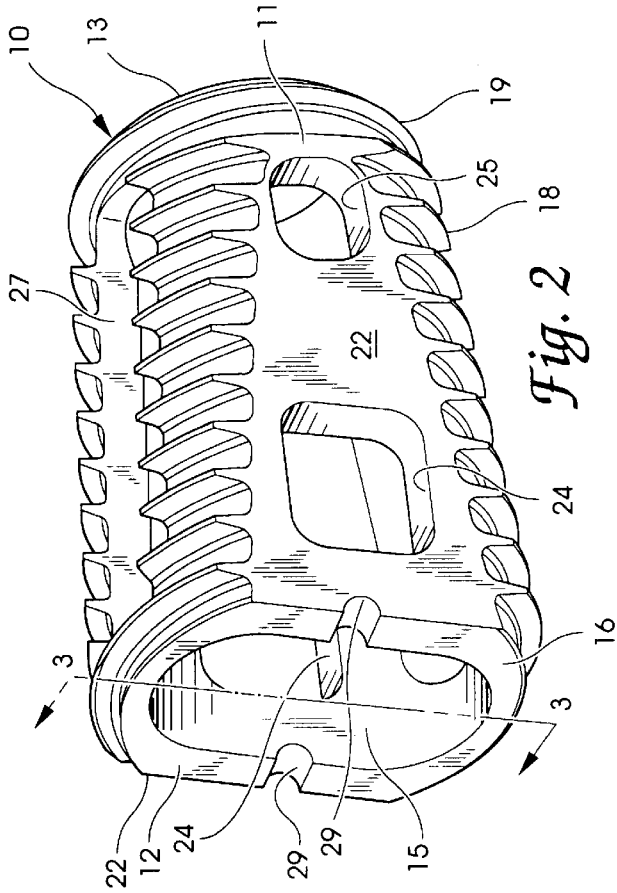
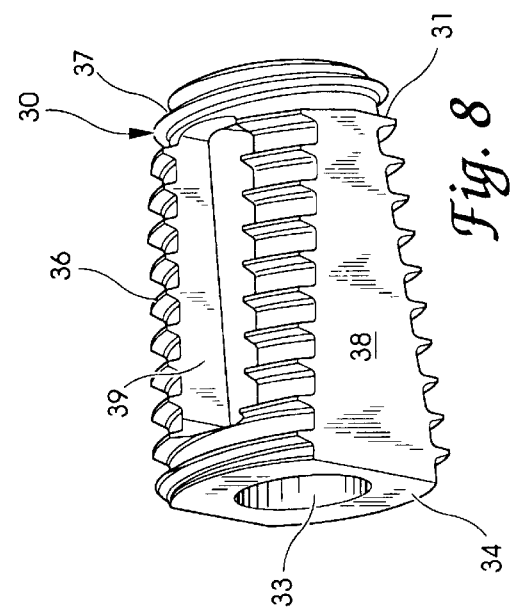

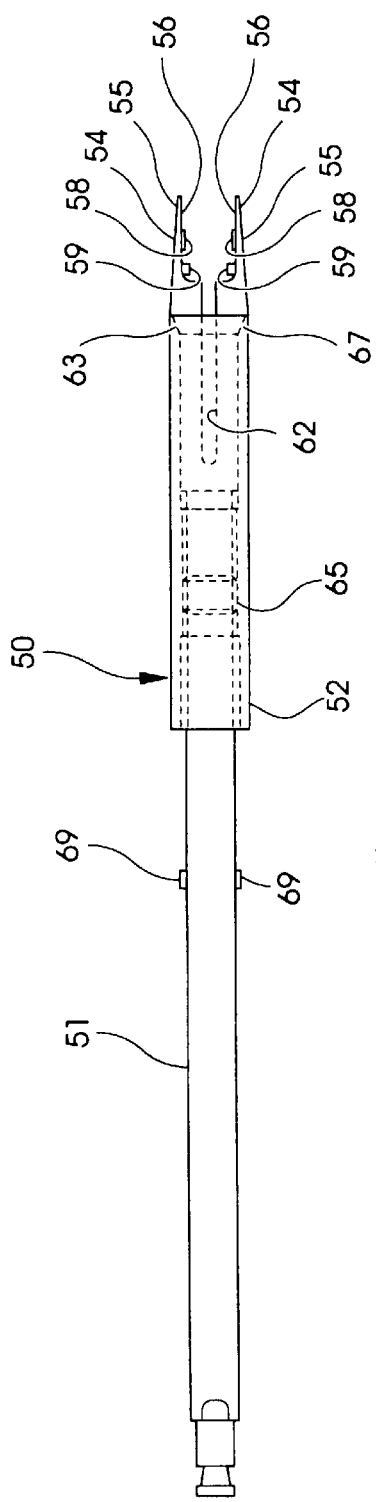
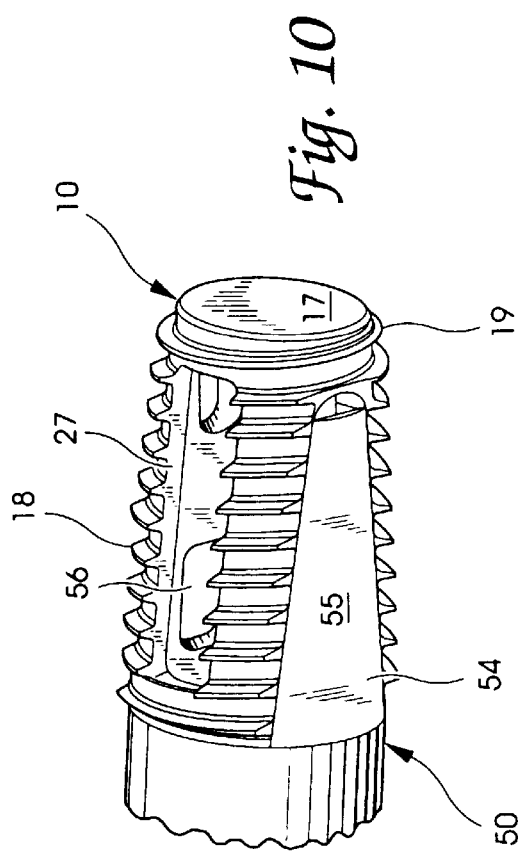

OSTEOGENIC FUSION DEVICES

The present application is a continuation-in-part of application, Ser. No. 08/413,353, filed on Mar. 30, 1995 now U.S. Pat. No. 5,669,909, which is a continuation-in-part of application Ser. No. 08/411,017, filed on Mar. 27, 1995 now U.S. Pat. No. 5,782,919, and is a continuation-in-part of application Ser. No. 08/482,038, filed on Jun. 7, 1995, which issued on Jul. 8, 1997, as U.S. Pat. No. 5,645,084.

BACKGROUND OF THE INVENTION

The present invention relates to an artificial implant to be placed into the intervertebral space left after the removal of a damaged spinal disc. Specifically, the invention concerns an implant that facilitates arthrodesis or fusion between adjacent vertebrae while also maintaining or restoring the normal spinal anatomy at the particular vertebral level.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intradiscal space, otherwise the space may collapse resulting in damage to the nerves extending along the spinal column.

In order to prevent this disc space collapse, the intradiscal space is filled with bone or a bone substitute in order to fuse the two adjacent vertebrae together. In early techniques, bone material was simply disposed between the adjacent vertebrae, typically at the posterior aspect of the vertebrae, and the spinal column was stabilized by way of a plate or a rod spanning the affected vertebrae. With this technique once fusion occurred the hardware used to maintain the stability of the segment became superfluous. Moreover, the surgical procedures necessary to implant a rod or plate to stabilize the level during fusion were frequently lengthy and involved.

It was therefore determined that a more optimum solution to the stabilization of an excised disc space is to fuse the vertebrae between their respective end plates, most optimally without the need for anterior or posterior plating. There have been an extensive number of attempts to develop an acceptable intradiscal implant that could be used to replace a damaged disc and yet maintain the stability of the disc interspace between the adjacent vertebrae, at least until complete arthrodesis is achieved. These "interbody fusion devices" have taken many forms. For example, one of the more prevalent designs takes the form of a cylindrical implant. These types of implants are represented by the patents to Bagby, U.S. Pat. No. 4,501,269; Brantigan, U.S. Pat. No. 4,878,915; Ray, U.S. Pat. Nos. 4,961,740 and 5,055,104; and Michelson, U.S. Pat. No. 5,015,247. In these cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intradiscal space and the vertebral end plates. These types of devices are represented by the patents to Brantigan, U.S. Pat. Nos. 4,743,256; 4,834,757 and 5,192,327.

In each of the above listed patents, the transverse cross section of the implant is constant throughout its length and is typically in the form of a right circular cylinder. Other implants have been developed for interbody fusion that do not have a constant cross section. For instance, the patent to McKenna, U.S. Pat. No. 4,714,469 shows a hemispherical implant with elongated protuberances that project into the vertebral end plate. The patent to Kuntz, U.S. Pat. No. 4,714,469, shows a bullet shaped prosthesis configured to optimize a friction fit between the prosthesis and the adjacent vertebral bodies. Finally, the implant of Bagby, U.S. Pat. No. 4,936,848 is in the form of a sphere which is preferably positioned between the centrums of the adjacent vertebrae.

Interbody fusion devices can be generally divided into two basic categories, namely solid implants and implants that are designed to permit bone ingrowth. Solid implants are represented by U.S. Pat. Nos. 4,878,915; 4,743,256; 4,349,921 and 4,714,469. The remaining patents discussed above include some aspect that permits bone to grow across the implant. It has been found that devices that promote natural bone ingrowth achieve a more rapid and stable arthrodesis. The device depicted in the Michelson patent is representative of this type of hollow implant which is typically filled with autologous bone prior to insertion into the intradiscal space. This implant includes a plurality of circular apertures which communicate with the hollow interior of the implant, thereby providing a path for tissue growth between the vertebral end plates and the bone or bone substitute within the implant. In preparing the intradiscal space, the end plates are preferably reduced to bleeding bone to facilitate this tissue ingrowth. During fusion, the metal structure provided by the Michelson implant helps maintain the patency and stability of the motion segment to be fused. In addition, once arthrodesis occurs, the implant itself serves as a sort of anchor for the solid bony mass.

A number of difficulties still remain with the many interbody fusion devices currently available. While it is recognized that hollow implants that permit bone ingrowth into bone or bone substitute within the implant is an optimum technique for achieving fusion, most of the prior art devices have difficulty in achieving this fusion, at least without the aid of some additional stabilizing device, such as a rod or plate. Moreover, some of these devices are not structurally strong enough to support the heavy loads and bending moments applied at the most frequently fused vertebral levels, namely those in the lower lumbar spine.

There has been a need for providing a hollow interbody fusion device that optimizes the bone ingrowth capabilities but is still strong enough to support the spine segment until arthrodesis occurs. It has been found by the present inventors that openings for bone ingrowth play an important role in avoiding stress shielding of the autologous bone impacted within the implant. In other words, if the ingrowth openings are improperly sized or configured, the autologous bone will not endure the loading that is typically found to be necessary to ensure rapid and complete fusion. In this instance, the bone impacted within the implant may resorb or evolve into simply fibrous tissue, rather than a bony fusion mass, which leads to a generally unstable construction. On the other hand, the bone ingrowth openings must not be so extensive that the cage provides insufficient support to avoid subsidence into the adjacent vertebrae.

The use of bone graft materials in past metal cage fusion devices has presented several disadvantages. Autograft is undesirable because it may not yield a sufficient quantity of graft material. The additional surgery to extract the autograft also increases the risk of infection and may reduce structural integrity at the donor site. Furthermore, many patients complain of significant pain for several years after the donor surgery. Although, the supply of allograft material is not so limited, allograft is also disadvantageous because of the risk of disease transmission and immune reactions. Furthermore, allogenic bone does not have the osteogenic potential of autogenous bone and therefore will provide only temporary support.

These disadvantages have led to the investigation of bioactive substances that regulate the complex cascade of cellular events of bone repair. Such substances include bone morphogenic proteins, for use as alternative or adjunctive graft materials. Bone morphogenic proteins (BMPs), a class of osteoinductive factors from bone matrix, are capable of inducing bone formation when implanted in a fracture or surgical bone site. Recombinantly produced human bone morphogenic protein-2 (rhBMP-2) has been demonstrated in several animal models to be effective in regenerating bone in skeletal defects.

SUMMARY OF THE INVENTION

In response to the needs still left unresolved by the prior devices, the present invention contemplates a hollow threaded interbody fusion device configured to restore the normal angular relation between adjacent vertebrae. In particular, the device includes an elongated body, tapered along substantially its entire length, defining a hollow interior and having an outer diameter greater than the size of the space between the adjacent vertebrae. The body includes an outer surface with opposite tapered cylindrical portions and a pair of opposite flat tapered side surfaces between the cylindrical portions. Thus, at an end view, the fusion device gives the appearance of a cylindrical body in which the sides of the body have been truncated along a chord of the body's outer diameter. The cylindrical portions are threaded for controlled insertion and engagement into the end plates of the adjacent vertebrae.

In another aspect of the invention, the outer surface is tapered along its length at an angle corresponding, in one embodiment, to the normal lordotic angle of lower lumbar vertebrae. The outer surface is also provided with a number of vascularization openings defined in the flat side surfaces, and a pair of elongated opposite bone ingrowth slots defined in the cylindrical portions. The bone ingrowth slots have a transverse width that is preferably about half of the effective width of the cylindrical portions within which the slots are defined.

In another embodiment, the interbody fusion device retains the same tapered configuration of the above embodiment, along with the truncated side walls and interrupted external threads. However, in this embodiment, the implant is not hollow but is instead solid. Bone ingrowth is achieved by forming the solid tapered implant of a porous high strength material that permits bone ingrowth into interconnected pores while retaining sufficient material for structural stability in situ. In one preferred embodiment, the material is porous tantalum.

In another aspect of this invention, a hollow interbody fusion device is provided with an osteogenic material to optimize fusion. The osteogenic material comprises an osteoinductive protein in a suitable carrier.

In still another embodiment, the interbody fusion device is solid instead of hollow and is composed of a porous high strength material that permits bone ingrowth into interconnected pores. In one preferred embodiment, the material is coated with an osteoinductive material.

DESCRIPTION OF THE FIGURES

FIG. 2 is an enlarged perspective view of an interbody fusion device according to one embodiment of the present invention.

FIG. 3 is a side cross-sectional view of the interbody fusion device shown in FIG. 2, taken along line 3—3 as viewed in the direction of the arrows.

FIG. 4 is an end elevational view from the anterior end of the interbody fusion device shown in FIG. 2.

FIG. 5 is a top-elevational view of the interbody fusion device shown in FIG. 2.

FIG. 8 is a perspective view of an alternative embodiment of the interbody fusion device according to the present invention.

FIG. 8A is a perspective view of another embodiment of a tapered interbody fusion device according to the present invention.

FIG. 9 is a top-elevational view of an implant driver according to another aspect of the present invention.

FIG. 10 is an enlarged perspective view of the end of the implant driver engaged about an interbody fusion device, as depicted in FIG. 2.

FIGS. 13(a)–12(d) show four steps of a method in accordance with one aspect of the invention for implanting the interbody fusion device, such as the device shown in FIG. 2.

DESCRIPTION OF THE PREFERRED EMBODIMENTS

Figure 1:
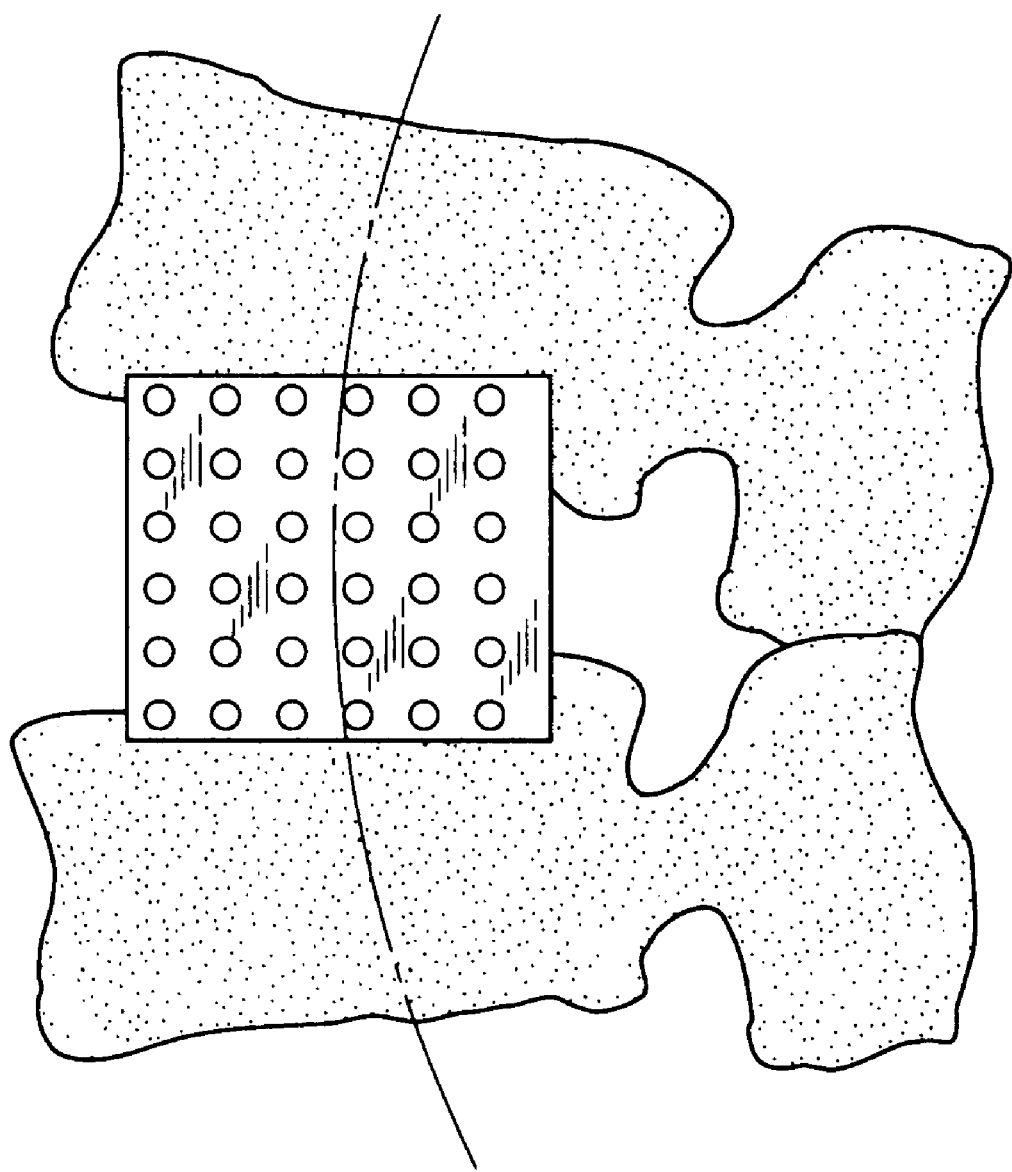
FIG. 1 is a side-elevational view in the sagittal plane of a fusion device of the prior art.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An interbody fusion device 10 in accordance with one aspect of the present invention is shown in FIGS. 2–5. The device is formed by a solid conical body 11, that is preferably formed of a biocompatible or inert material. For example, the body 11 can be made of a medical grade stainless steel or titanium, or other suitable material having adequate strength characteristics set forth herein. The device may also be composed of a biocompatible porous material, such as porous tantalum provided by Implex Corp. For purposes of reference, the device 10 has an anterior end 12 and a posterior end 13, which correspond to the anatomic position of the device 10 when implanted in the intradiscal space. The conical body 11 defines a hollow interior 15 which is bounded by a body wall 16 and closed at the posterior end 13 by an end wall 17 (see FIG. 3). The hollow interior 15 of the device 10 is configured to receive autograft bone or a bone substitute material adapted to promote a solid fusion between adjacent vertebrae and across the intradiscal space.

In accordance with the invention, the interbody fusion device 10 is a threaded device configured to be screw threaded into the end plates of the adjacent vertebrae. In one embodiment of the invention, the conical body 11 defines a series of interrupted external threads 18 and a complete thread 19 at the leading end of the implant. The complete thread 19 serves as a "starter" thread for screwing the implant into the vertebral endplates at the intradiscal space. The threads 18 and 19 can take several forms known in the art for engagement into vertebral bone. For instance, the threads can have a triangular cross-section or a truncated triangular cross-section. Preferably, the threads have a height of 1.0 mm (0.039 in) in order to provide adequate purchase in the vertebral bone so that the fusion device 10 is not driven out of the intradiscal space by the high loads experienced by the spine. The thread pitch in certain specific embodiments can be 2.3 mm (0.091 in) or 3.0 mm (0.118 in), depending upon the vertebral level at which the device 10 is to be implanted and the amount of thread engagement necessary to hold the implant in position.

In one aspect of the invention, the conical body 11, and particularly the body wall 16, includes parallel truncated side walls 22, shown most clearly in FIG. 4. The side walls are preferably flat to facilitate insertion of the fusion device between the end plates of adjacent vertebrae and provide area between for bony fusion. The truncated side walls extend from the anterior end 12 of the device up to the complete threads 19 at the posterior end 13. Thus, with the truncated side walls 22, the device 10 gives the appearance at its end view of an incomplete circle in which the sides are cut across a chord of the circle. In one specific example, the interbody fusion device 10 has a diameter at its anterior end of 16.0 mm (0.630 in). In this specific embodiment, the truncated side walls 22 are formed along parallel chord lines approximately 12.0 mm (0.472 in) apart, so that the removed arc portion of the circle roughly subtends 90° at each side of the device. Other benefits and advantages provided by the truncated side walls 22 of the fusion device 10 will be described in more detail herein.

The conical body 11 of the device 10 includes a pair of vascularization openings 24 and 25 defined through each of the truncated side walls 22. These openings 24 and 25 are adapted to be oriented in a lateral direction or facing the sagittal plane when the fusion device is implanted within the intradiscal space. The openings are intended to provide a passageway for vascularization to occur between the bone implant material within the hollow interior 15 and the surrounding tissue. In addition, some bone ingrowth may also occur through these openings. The openings 24 and 25 have been sized to provide optimum passage for vascularization to occur, while still retaining a significant amount of structure in the conical body 11 to support the high axial loads passing across the intradiscal space between adjacent vertebrae.

The conical body 11 also defines opposite bone ingrowth slots 27, each of which are oriented at 90° to the truncated side walls 22. Preferably, these slots 27 are directly adjacent the vertebral end plates when the device 10 is implanted. More particularly, as the threads 18 and 19 of the device are screwed into the vertebral endplates, the vertebral bone will extend partially into the slots 27 to contact bone implant material contained within the hollow interior 15 of the device 10. As shown more clearly in FIG. 5, the bone ingrowth slots 27 are configured to provide maximum opening for bone ingrowth, in order to ensure complete arthrodesis and a solid fusion. Preferably, the slots have a lateral width that approximates the effective width of the threaded portions of the body.

It has been found that the prior devices which utilize a plurality of small apertures do not promote a rapid and solid arthrodesis of the bone material. Instead, the smaller apertures often lead to pseudo-arthrosis and the generation of fibrous tissue. Since the bone ingrowth slots 27 of the present invention are directly facing the vertebrae, they are not situated in a portion of the device that must bear high loads. Instead, the truncated side walls 22 will bear most of the load passing between the vertebral end plates through the interrupted threads 18 and across the intradiscal space.

In a further feature, the anterior end 12 of the body wall 16 can define a pair of diametrically opposed notches 29, which are configured to engage an implant driver tool as described herein. Moreover, the end wall 17 at the posterior end 13 of the implant can be provided with a tool engagement feature (not shown). For example, a hex recess can be provided to accommodate a hex driver tool, as described further herein.

In one important feature of the interbody fusion device of the present invention, the body 11 includes a tapered or conical form. In other words, the outer diameter of the device at its anterior end 12 is larger than the outer diameter at the posterior end 13. As depicted in FIG. 3, the body wall 16 tapers at an angle A about the centerline CL of the device 10. The taper of the body wall 16 is adapted to restore the normal relative angle between adjacent vertebrae. For example, in the lumbar region, the angle A is adapted to restore the normal lordotic angle and curvature of the spine in that region. In one specific example, the angle A is 8.794°. It is understood that the implant may have non-tapered portions, provided that the portions do not otherwise interfere with the function of the tapered body.

Figure 7:
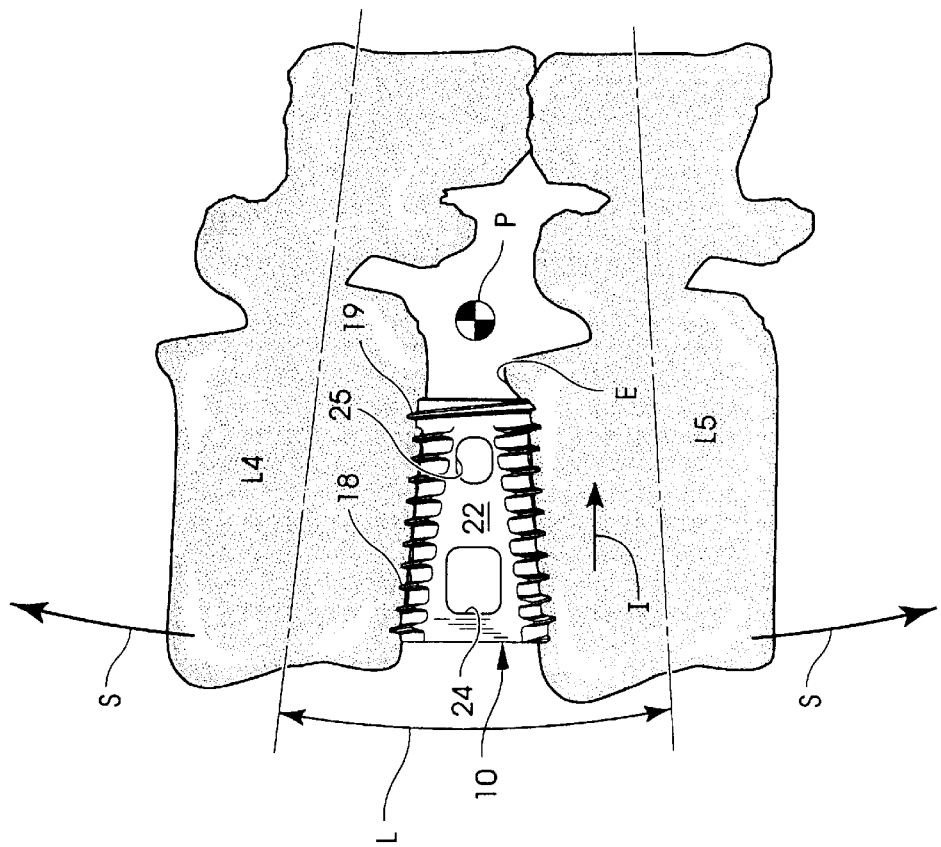
FIG. 7 is a sagittal plane view of the interbody fusion device implanted between L4 and L5 shown in FIG. 6.

The taper angle A of the implant, coupled with the outer diameter at the anterior and posterior ends of the fusion device 10, define the amount of angular spreading that will occur between the adjacent vertebrae as the implant is placed or screwed into position. This feature is depicted more clearly in FIGS. 6 and 7 in which a preferred construct employing a pair of fusion devices 10 is shown. In the depicted construct, the devices 10 are disposed between the lower lumbar vertebrae L4 and L5, with the threads 18 and 19 threaded into the end plates E of the two vertebrae. As shown in FIG. 7, as the device 10 is threaded into the end plates E, it advances in the direction of the arrow I toward the pivot axis P of the vertebral level. The pivot axis P is nominally the center of relative rotation between the adjacent vertebrae of the motion segment. As the tapered fusion device 10 is driven further in the direction of the arrow I toward the pivot axis P, the adjacent vertebrae L4 and L5 are angularly spread in the direction of the arrows S. Depth of insertion of the fusion device 10 will determine the ultimate lordotic angle L achieved between the two vertebrae.

In specific embodiments of the implant 10, the outer diameter or thread crest diameter at the anterior end 12 can be 16, 18 or 20 mm, and the overall length of the device 26 mm. The sizing of the device is driven by the vertebral level into which the device is implanted and the amount of angle that must be developed.

Figure 6:
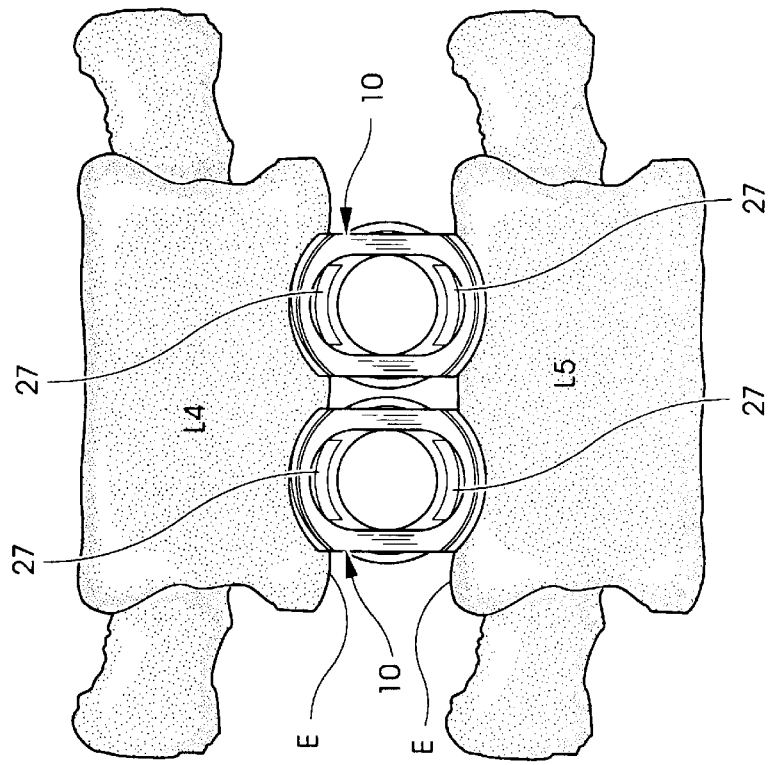
FIG. 6 is an A-P lateral view from the anterior aspect of the spine showing two interbody fusion devices according to FIG. 2 implanted within the interbody space between L4 and L5.
Figure 11:
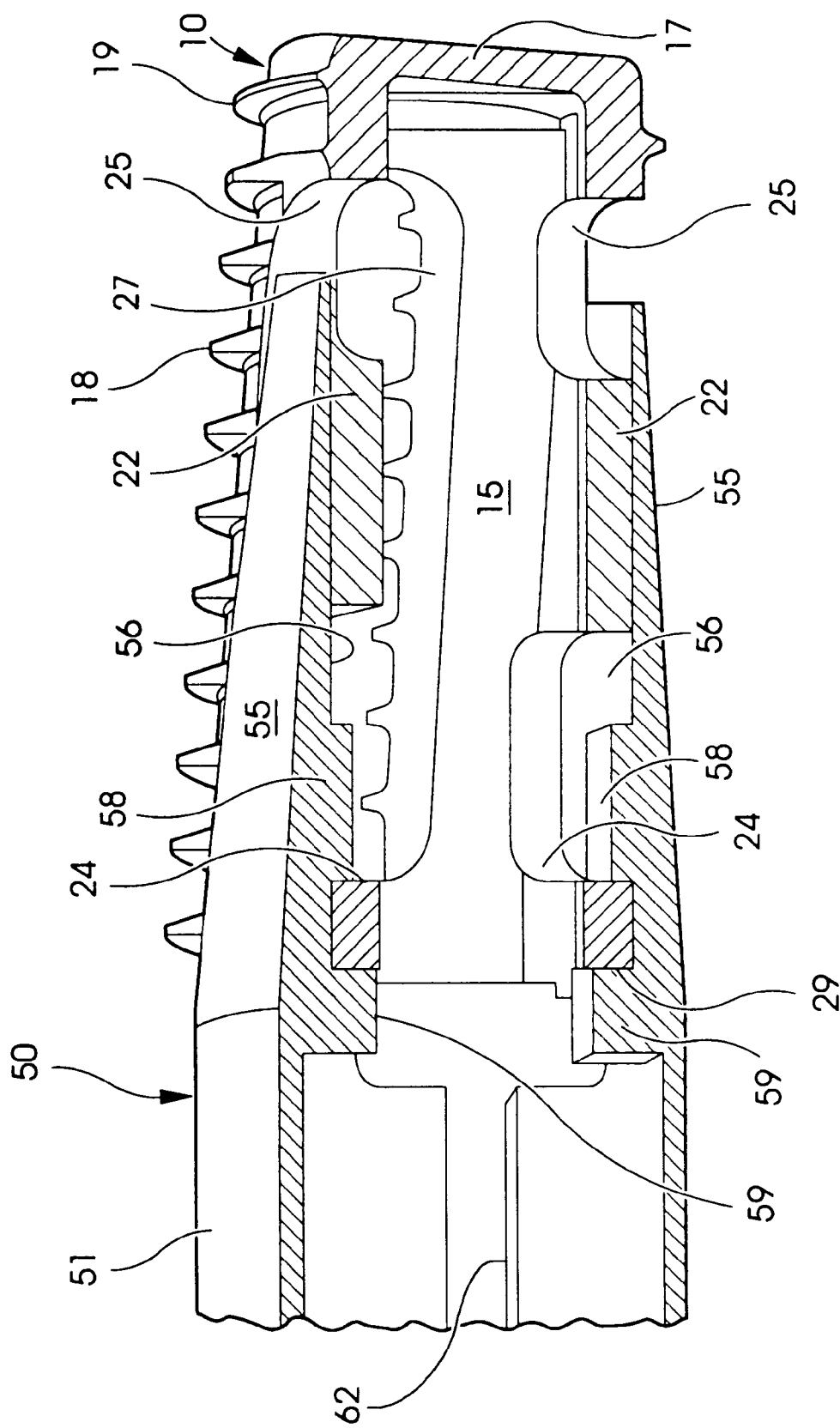
FIG. 11 is an enlarged partial side cross-sectional view showing the implant driver engaging the interbody fusion device, as shown in FIG. 10.
Figure 12:
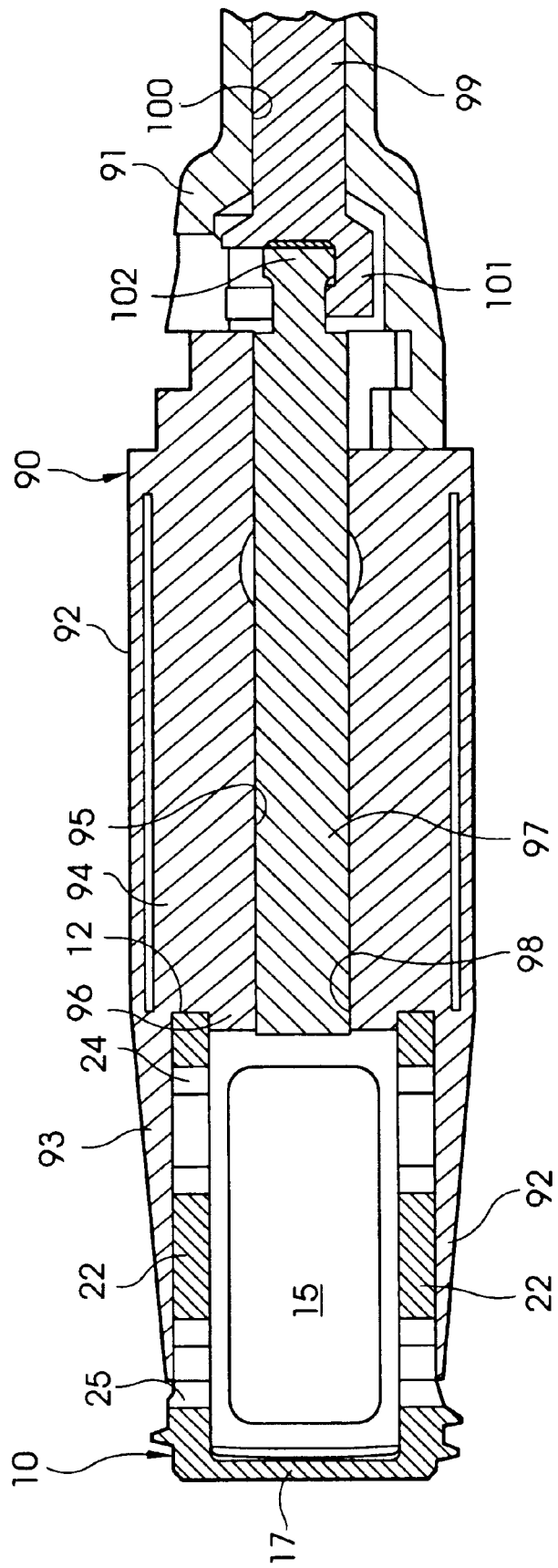
FIG. 12 is an enlarged partial side cross-sectional view showing an implant driver of an alternative embodiment adapted for engaging the interbody fusion device 10.
Figure 13A:
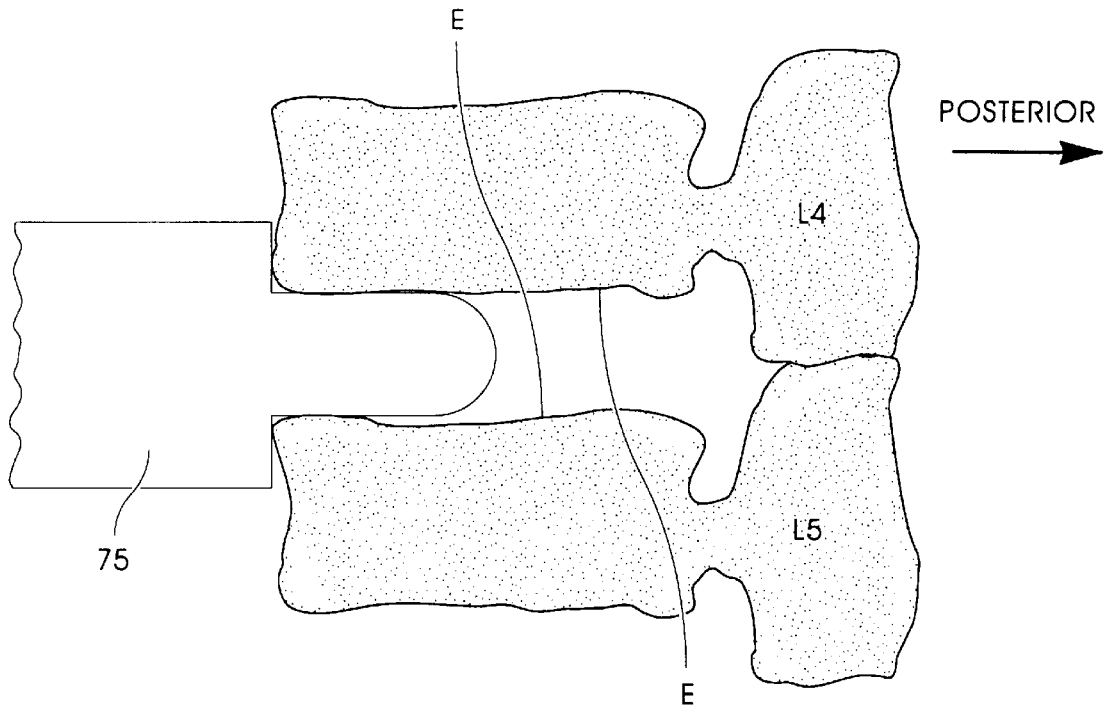
Figure 13B:
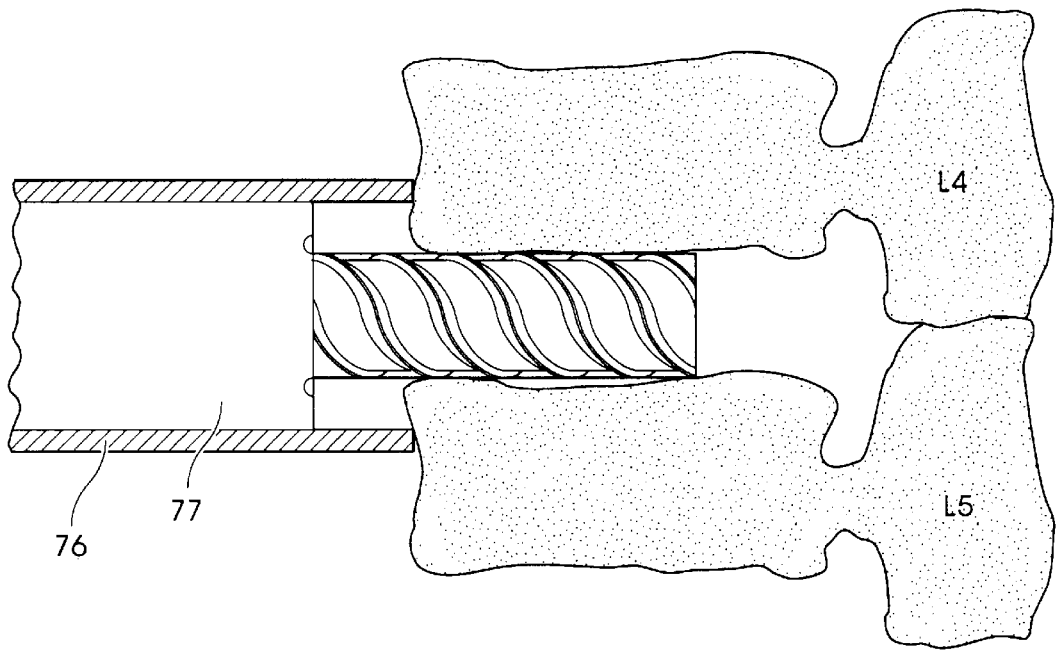
Figure 13C:
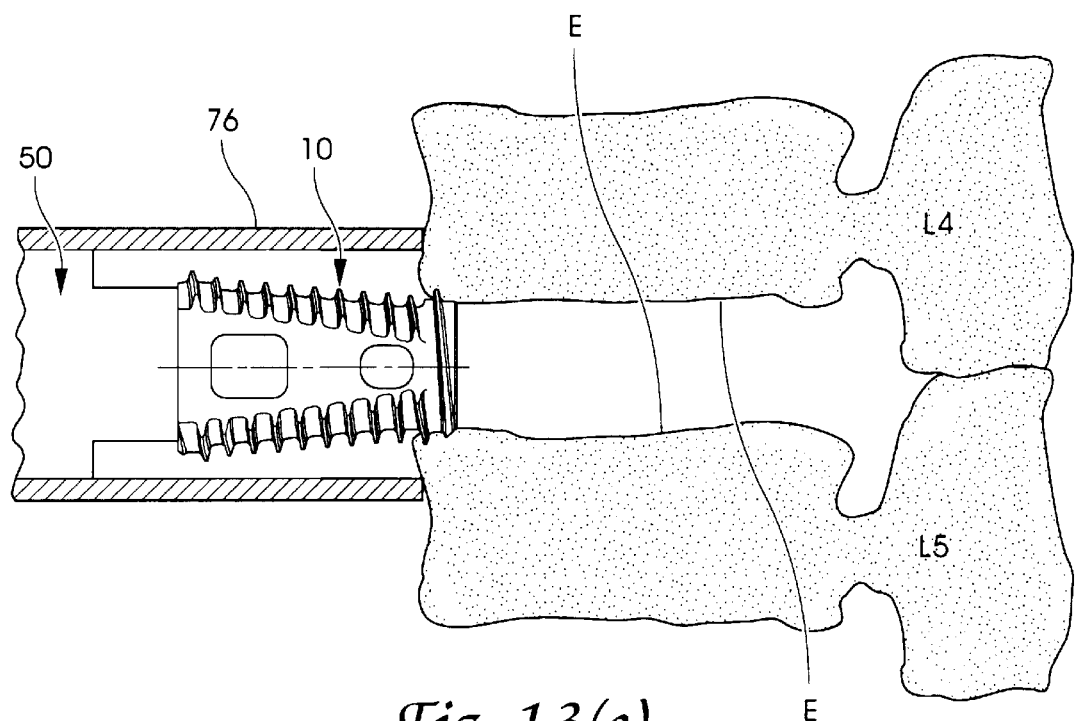
Figure 13D:
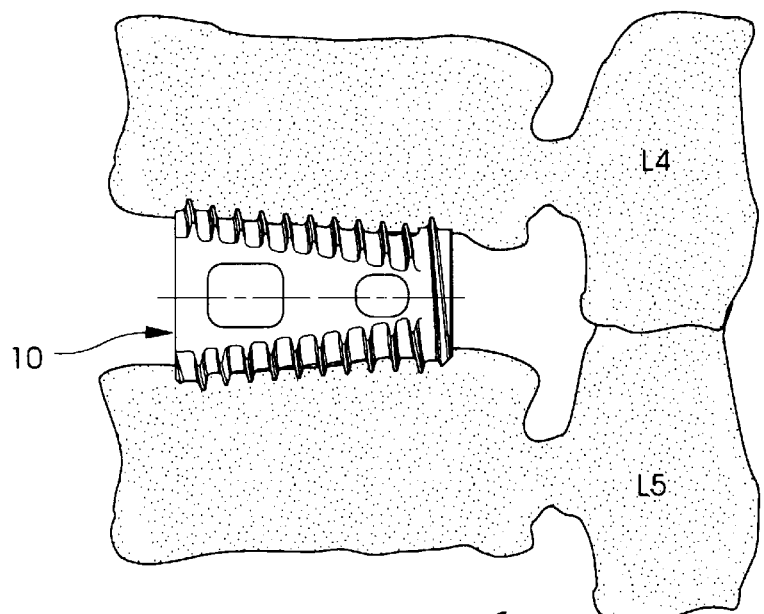
FIGS. 14(a)–13(d) depict steps of an alternative method for implanting the interbody fusion device, such as the device shown in FIG. 2.
Figure 14A:
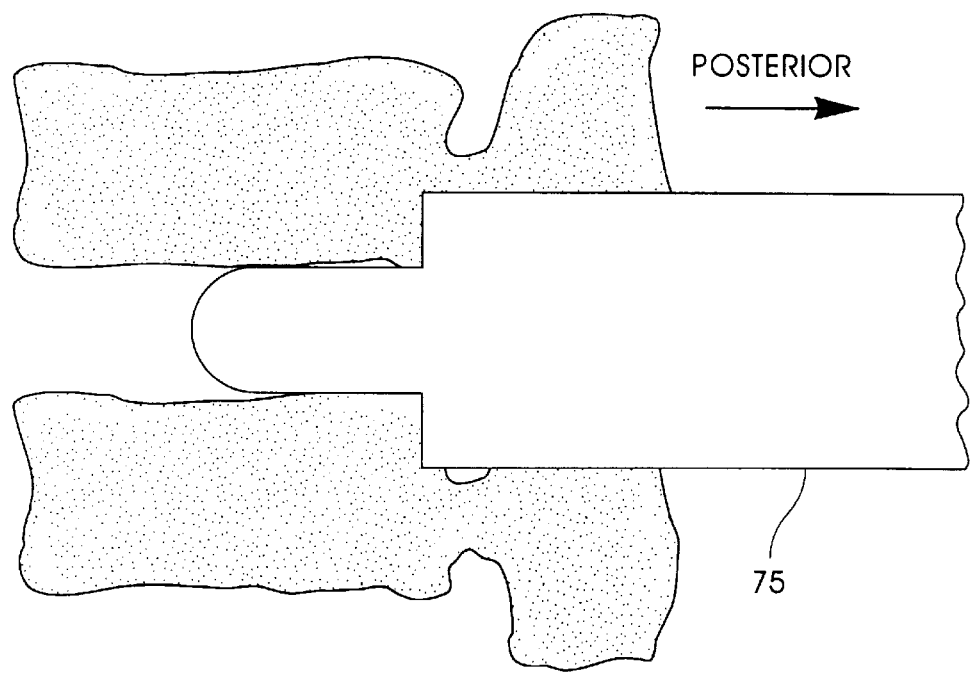
Figure 14B:
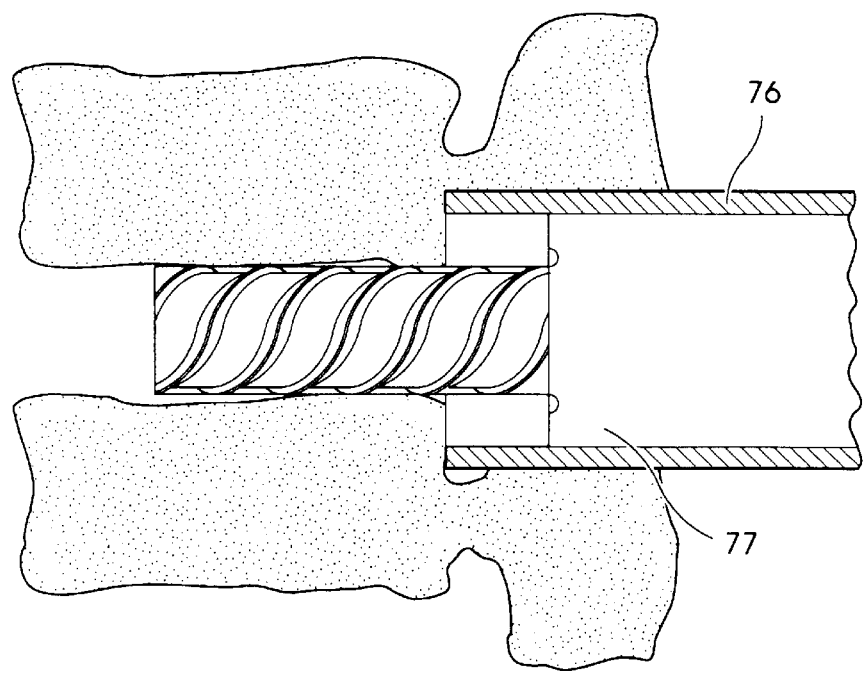
Figure 14C:
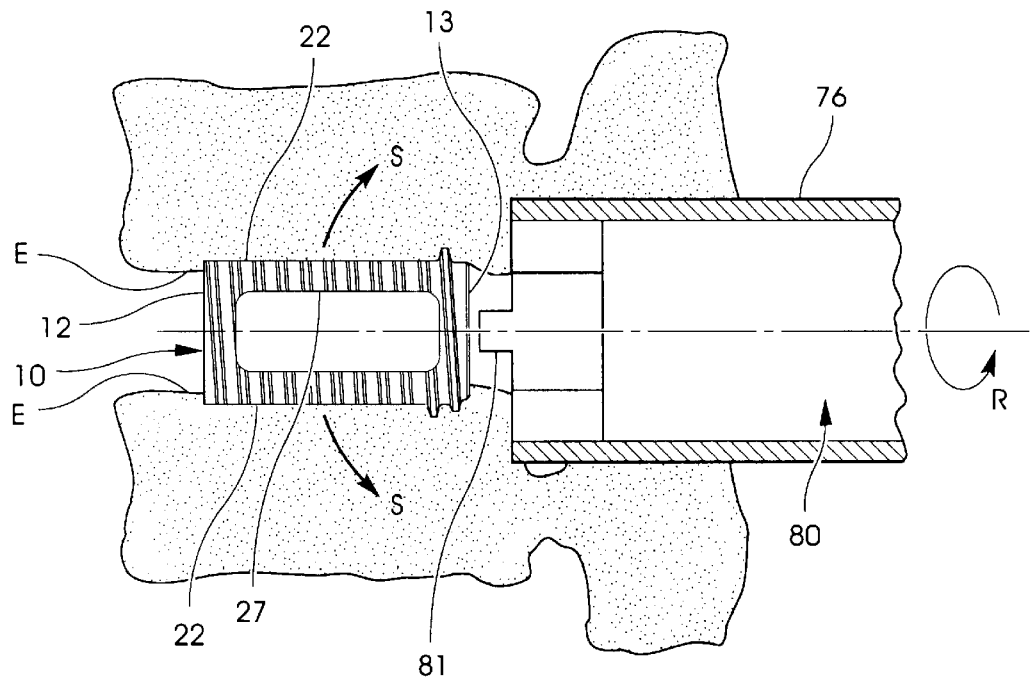
Figure 14D:
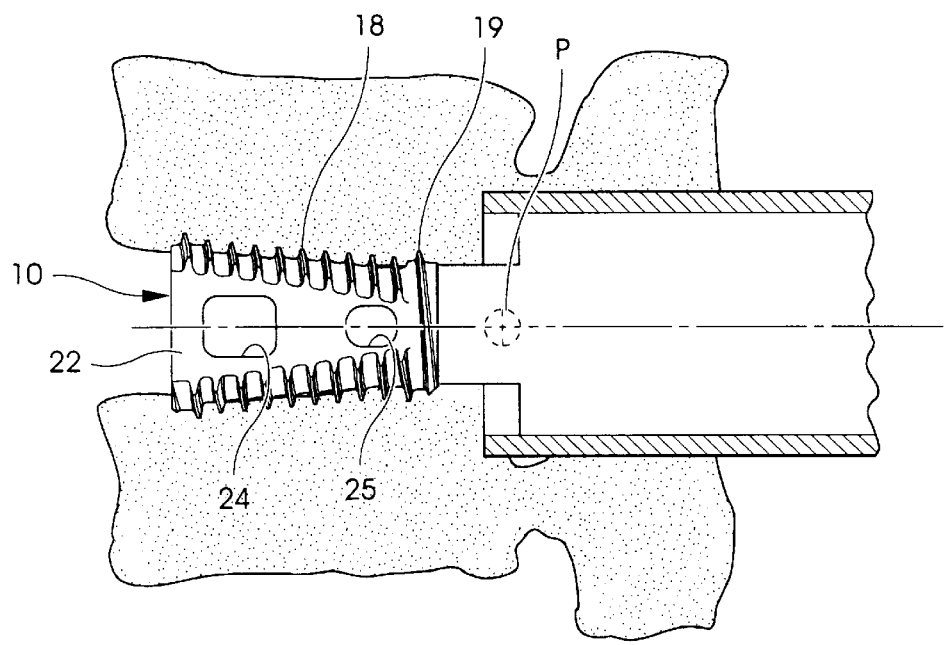

In another aspect of the invention, device 10 is sized so that two such cylindrical bodies 11 can be implanted into a single disc space, as shown in FIG. 6. This permits the placement of additional bone graft material between and around the devices 10 in situ. This aspect further promotes fusion across the intradiscal space and also serves to more firmly anchor the devices between the adjacent vertebrae to prevent expulsion due to the high axial loads at the particular vertebral level.

In one specific embodiment of the interbody fusion device 10, the vascularization opening 24 is generally rectangular in shape having dimensions of 6.0 mm (0.236 in) by 7.0 mm (0.276 in). Similarly, the vascularization opening 25 is rectangular with dimensions of 4.0 mm (0.157 in) by 5.0 mm (0197 in). Naturally, this opening is smaller because it is disposed at the smaller posterior end 13 of the device 10. The bone ingrowth slots 27 are also rectangular in shape with a long dimension of 20.0 mm (0.787 in) and a width of 6.0 mm (0.236 in). It has been found that these dimensions of the vascularization openings 24, 25 and slots 27 provide optimum bone ingrowth and vascularization. In addition, these openings are not so large that they compromise the structural integrity of the device or that they permit the bone graft material contained within the hollow interior 15 to be easily expelled during implantation.

As can be seen in FIG. 7, when the device is in position between the L4 and L5 vertebrae, the vascularization openings 24 and 25 are side facing to contact the highly vascularized tissue surrounding the vertebrae. In addition, as can be seen in FIG. 6, the bone ingrowth slots 27 are axially directed so that they contact the vertebral end plates E.

In an alternative embodiment of the invention, shown in FIG. 8, an interbody fusion device 30 is formed of a conical body 31. The body wall 34 defines a hollow interior 33 as with the fusion device 10 of the previous embodiment. However, in this embodiment the truncated side wall 38 does not include any vascularization openings. Moreover, the bone ingrowth slots 39 on opposite sides of the device 30 are smaller. This means that the interrupted threads 36 on the exterior of the device 30 extend a greater length around the implant. Such a design could be utilized if a porous material (e.g., porous tantalum) were used to provide additional surface area for tissue ingrowth and anchorage to the adjacent bone. Also, this interbody fusion device 30 of the embodiment shown in FIG. 8 can have application at certain vertebral levels where the risk of expulsion of the device is greatest. Consequently, the amount of thread contact is increased to prevent such expulsion. Prior to insertion, the hollow interior 15 of the fusion device 10 is filled completely with bone or substitute to facilitate this pre-loading.

In a further embodiment using a porous material, the interbody fusion device 110 of FIG. 8A retains the tapered configuration of the previous embodiments, but is solid instead of hollow. The device 110 comprises a tapered body 111 having a larger outer diameter at is anterior end 112 than at is posterior end 113. The entire body 111 is solid leaving a closed surface, such as surface 115, at both ends of the implant. The device includes the interrupted threads 118, starter threads 119 and truncated side walls 122 of the prior embodiments. A driving tool slot 129 can also be defined in the end surface 115. Alternatively, the starter threads 119 can be eliminated leaving an unthreaded cylindrical portion at the posterior end of the implant. Similarly, the driving tool slot 129 take on many configurations depending upon the design of the tool used to insert the device 110 into the intradiscal space.

The benefits of the embodiment of the fusion device shown in FIG. 8A are especially appreciated by the use of a porous, high strength material to form the solid body 111. In the preferred embodiment, this material is a porous tantalum-carbon composite marketed by Implex Corp. under the tradename HEDROCEL® and described in U.S. Pat. No. 5,282,861 to Kaplan, which description is incorporated herein by reference. Due to the nature of the HEDROCEL® material, the entire exterior surface of the solid body 111 includes pores 130 that are interconnected throughout the body. The substrate of the HEDROCEL® carbon-tantalum composite is a skeleton of vitreous carbon, or a reticulated open cell carbon foam, which defines a network of interconnecting pores. The substrate is infiltrated with vapor-deposited thin film of a metallic material. The metallic material is preferably a Group VB transition metal such as tantalum, niobium or alloys thereof.

HEDROCEL® is preferred because it provides the advantages of both metal and ceramic implants without the corresponding disadvantages. HEDROCEL® is well suited for the interbody fusion device of the present invention because it mimics the structure of bone and has a modulus of elasticity that approximates that of human bone. The interconnected porosity encourages bone ingrowth and eliminates dead ends which limit vascularization of the bone. The infiltrated metal film provides strength and stiffness without significant weight increase. A HEDROCELO® implant is sufficiently strong to maintain the intervertebral space and normal curvature of the spine at the instrumented motion segment. At the same time, stress shielding is avoided. This composite material is also advantageous because it eliminates the need for allografts or autografts An additional advantage of this material is that it does not undergo resorption. This prevents early degradation which can inhibit bone regeneration. A non-resorbable implant is also beneficial where complete bone ingrowth may not be achieved. Disadvantages of permanent, non-resorbable implants, however, are avoided because of the excellent biocompatibility and osteoconductivity of the composite.

While HEDROCEL® is preferred, it is contemplated that any suitable high strength porous material may be used. Other open-celled substrates and metals are contemplated. For example, the substrate may be other carbonaceous materials, such as graphite, or ceramics, such as tricalcium phosphate or calcium aluminate. Any suitable metal is contemplated, but Group VB elements, such as tantalum and niobium, and their alloys, are preferred. Tantalum is particularly preferred for its good mechanical properties and biocompatibility.

During a surgical implantation procedure, the surgeon may apply an osteogenic material to a fusion device 10 or 30 by packing the hollow interior 15 with an osteogenic material. Alternatively, in the case of a fusion device such as device 30, the osteogenic material can be applied by introducing an osteogenic composition to the pores of the bone ingrowth material. Any suitable osteogenic material or composition is contemplated. The osteogenic compositions preferably comprise a therapeutically effective amount of a bone inductive factor such as a bone morphogenic protein in a pharmaceutically acceptable carrier.

For the osteogenic compositions, any suitable carrier which provides a vehicle for introducing the osteogenic material into the pores of the bone ingrowth material or the hollow interior of the device is contemplated. Such carriers are well known and commercially available.

The choice of carrier material is based on biocompatibility, biodegradability, mechanical properties and interface properties. The particular application of the compositions of the invention will define the appropriate formulation. The carrier may be any suitable carrier capable of delivering the proteins to the implant. Most preferably, the carrier is capable of being resorbed into the body. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfate, tricalcium phosphate (TCP), hydroxyapatite (HA), biphasic TCP/HA ceramic, polylactic acids and polyanhydrides. Other potential materials are biodegradable and biologically well defined, such as bone or dermal collagen. Further matrices are comprised of pure proteins or extracellular matrix components. The osteoinductive material may also be an admixture of the osteoinductive cytokine and a polymeric acrylic ester carrier. The polymeric acrylic ester can be polymethylmethacrylic.

Figure 16:
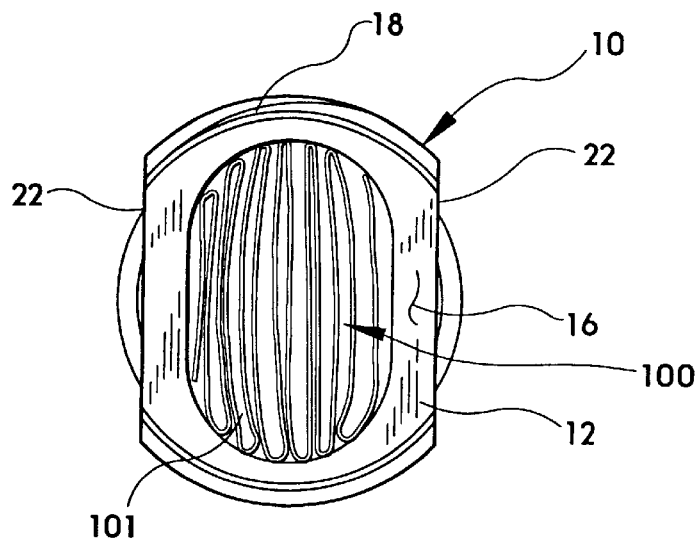
FIG. 16 is a side cross-sectional view of the interbody fusion device shown in FIG. 15, taken along line 16—16 as viewed in the direction of the arrows.
Figure 15:
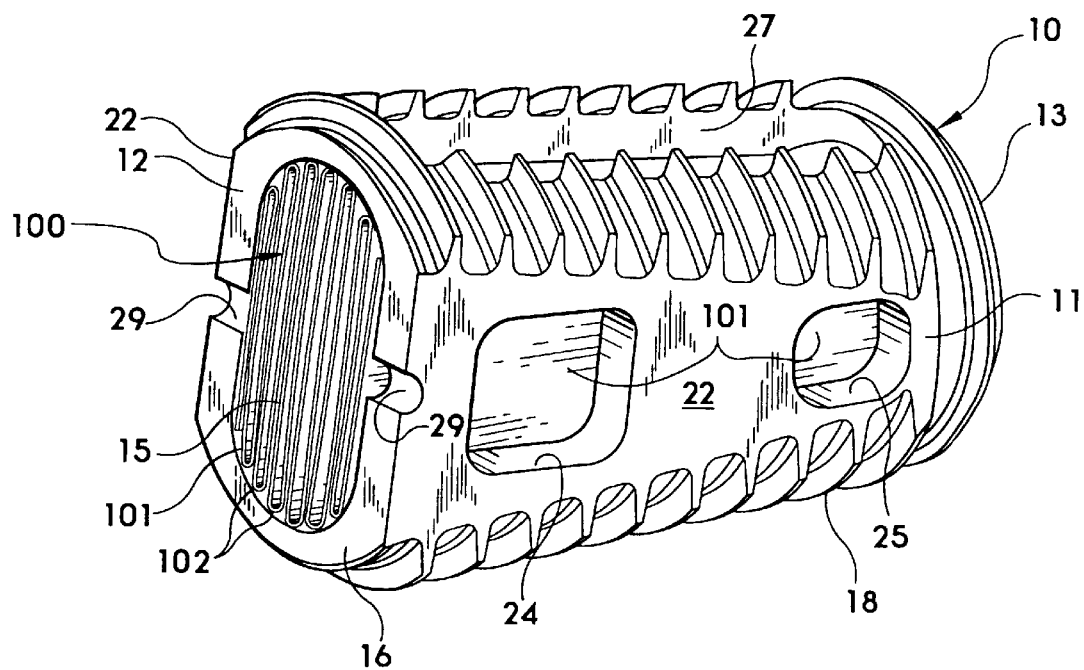
FIG. 15 is an enlarged perspective view of an interbody fusion device having an osteogenic material in the hollow interior according to one embodiment of the present invention.

For the hollow fusion devices, such as device 101, the carriers are preferably provided in strips or sheets which may be folded to conform to the hollow interior 15 as shown in FIGS. 15 and 16. It may be preferable for the carrier to extend out of openings of the devices, such as the vascularization openings 24, 25, to facilitate contact of the osteogenic material with the highly vascularized tissue surrounding the vertebrae. In one embodiment, the osteogenic material 100 includes a polylactic acid polymer acting as a carrier for a bone morphogenic protein, such as BMP-2. In this specific embodiment, the osteogenic material 100 is in the form of a sheet 101 that is overlapped at folds 102 within the hollow interior 15 of the device 10. Preferably, the sheet 101 is long enough so that when it is folded within the device 10 it substantially completely fills the hollow interior and extends at least partially into the vascularization openings 24 and 25.

As shown in FIGS. 15 and 16, the sheet 101 is folded generally parallel with the truncated side walls 22 so that the folds 102 of the sheet 101 are disposed adjacent the slots 27 in the threaded portion of the device. Alternatively, the sheet 101 can be folded so that the layers between the folds are generally perpendicular to the side walls 22. In this instance, the sheet 101 may extend at least partially into the slots 27.

The osteogenic material 100 can also be provided in several strips sized to fit within the hollow interior 15 of the fusion device 10. The strips (not shown) can be placed one against another to fill the interior. As with the folded sheet 101, the strips can be arranged within the device 10 in several orientations, such as with the surface of the strips directed either toward the vascularization openings 24, 25 or toward the slots 27. Preferably, the osteogenic material 100, whether provided in a single folded sheet or in several overlapping strips, has a length corresponding to the length of the hollow interior 15 of the device 10 and a width corresponding to the width of the device transverse to its longitudinal axis.

The choice of carrier is based on biocompatibility, biodegradability, mechanical properties and interface properties. The particular application of the compositions of the invention will define the appropriate formulation. The carrier may be any suitable carrier capable of delivering the proteins to the spacer.

As discussed in the Kaplan patent, the open cell tantalum material provides highly interconnected three-dimensional porosity that encourages bone ingrowth. Kaplan type materials facilitate bone ingrowth throughout the entire device for complete fusion and have the strength of metal without the disadvantages of metal such as stress shielding and incomplete fusion. An additional benefit of the porosity of these materials is that a bone growth inducing composition can be introduced into the pores. For example, in one embodiment, the composition includes a bone morphogenic protein in a liquid carrier which can be introduced into the pores to promote fusion. BMPs have been found to significantly reduce the time required to achieve arthrodesis and fusion across an instrumented disc space. Most preferably, the bone morphogenic protein is a BMP-2, such as recombinant human BMP-2. However, any bone morphogenic protein is contemplated including bone morphogenic proteins designated as BMP-1 through BMP-13. BMPs are commercially available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al.

The BMP may be provided in freeze-dried form and reconstituted in sterile water or another suitable medium or carrier. The carrier may be any suitable medium capable of delivering the proteins to the implant. Preferably the medium is supplemented with a buffer solution as is known in the art. The bone growth inducing composition can be introduced into the pores in any suitable manner. For example, the composition may be injected into the pores of the implant. In other embodiments, the composition is dripped onto the biocompatible material or the biocompatible material is soaked in the composition. In one specific embodiment of the invention, rhBMP-2 is suspended or admixed in a liquid carrier, such as water or liquid collagen. The liquid can be dripped into the device or the device can be immersed in a suitable quantity of the liquid, in either case for a period of time sufficient to allow the liquid to invade all of the interconnected pores throughout the pore material of the device.

In some cases, a BMP-bonding agent is applied to the porous biocompatible material of the implant prior to introduction of the BMP so that the agent can coat the pores of the device. Preferably, the agent is a calcium phosphate composition. It has been discovered that the rate of delivery of bone morphogenic proteins to the fusion site can be controlled by the use of such agents. The calcium phosphate compositions are thought to bond with the bone morphogenic protein and prevent the BMP from prematurely dissipating from the device before fusion can occur. It is further believed that retention of the BMP by the agent permits the BMP to leach out of the device at a rate that is conducive to complete and rapid bone formation and ultimately, fusion across the disc space. Any suitable, biocompatible calcium phosphate composition is contemplated. In a preferred embodiment, a layer of hydroxyapatite several microns thick is applied to the Kaplan material. The hydroxyapatite covers the tantalum film-covered ligaments while leaving the pores open. Also contemplated are tricalcium phosphate ceramics and hydroxyapatite/tricalcium phosphate ceramics.

The calcium phosphate composition may be applied to the porous biocompatible material of the implant in any suitable manner such as plasma spraying or chemical dipping where the porous material is dipped into a slurry of calcium phosphate composition. Methods for applying a coating of calcium phosphate compositions are described in the following: U.S. Pat. No. 5,164,187 to Constantz et al., U.S. Pat. No. 5,030,474 to Saita et al, U.S. Pat. No. 5,330,826 to Taylor et al, U.S. Pat. No. 5,128,169 to Saita et al, Re. 34,037 to Inoue et al, U.S. Pat. No. 5,068,122 to Kokubo et al, and U.S. Pat. Nos. 5,188,670 and 5,279,831 to Constantz which are hereby incorporated by reference.

EXAMPLE 1

Surgical Technique: Twenty-one mature female Alpine goats were used in this study. The goats weighed between 42 and 62 kilograms. All the goats underwent a surgical procedure under general endotracheal anesthesia using intravenous valium and ketamine for induction, and inhalation halothane for maintenance anesthesia. The anterior neck was prepped in a sterile fashion and a right anterolateral approach to the cervical spine was carried out through a longitudinal skin incision. The well developed longus coli muscle was incised in the midline, and the disc spaces at C2-C3, C3-C4, and C4-C5 exposed. Anterior cervical discectomies were carried out at each level by first excising the soft disc. An 8 mm distraction plug centered on a post was then tapped into the disc space providing distraction of the space. A working tube was then passed over the post and prongs at the end of the tube tapped into the vertebral bodies above and below the disc space. These prongs maintained distraction of the disc space as the centering post and distraction plug were removed. The disc space and vertebral bodies/endplates were then reamed with a 10 mm reamer through the working tube. The bone reamings were saved and used as graft materials. The reamed channel was then tapped followed by insertion of a 10 millimeter-diameter titanium BAK device (SpineTech, Minneapolis, Minn.). No attempt was made to excise the posterior longitudinal ligament or expose the spinal canal.

The goats were divided into three treatment groups consisting of seven goats each. Group I had a device filled with autogenous bone graft harvested from the reamings at each disc level. Group II utilized a hydroxyapatite-coated implant filled with autogenous bone reamings as graft. Group III utilized a device filled with a collagen sponge impregnated with 200 μg of recombinant BMP-2 (Genetics Institute, Cambridge, Mass.). Prior to installation of the devices, wounds were irrigated with a solution of normal saline, bacitracin (50 U/cc), polymyxin B (0.05 mg/cc), and neomycin (0.5%). The longus coli muscle was then closed with a running suture. The subcutaneous tissue was reapproximated with interrupted sutures and the skin with a running suture.

Post-operatively the animals were maintained under observation until fully recovered from general anesthesia. They received two doses of Naxcell (ceftiofur), 500 mg intravenously properatively and 500 mg intramuscularly post-operatively. A soft bandage was applied to the animals neck, and they were allowed ad lib activity under daily observation in a pen for several days.

Clinical evaluation was performed every three weeks. Lateral cervical spine radiographs were obtained immediately post-operatively and at three, six and nine weeks. Fluorochrome labels were administered at three, six and nine weeks. These consisted of oxytetracycline (30 mg/kg IV) at three weeks, alizarin complex one (30 mg/kg IV) at six weeks, and DCAF (20 mg/kg IV) at nine weeks. At twelve weeks, the goats were euthanized by an intravenous injection of Beuthanasia. The cervical spine was then excised, and all surrounding tissues removed from it. The specimen was then radiographed in the AP and lateral planes.

Biomechanical Testing: The spine specimens were brought fresh to the biomechanics laboratory for biomechanical testing. The spines were mounted into frames at C2 and C7 with a polyester resin (Lite Weight 3 Fiberglass-Evercoat, Cincinnati, Ohio). The biomechanical tests were performed on a modified MTS Bionix 858 Servo-Hydraluic Material Tester (MTS Corporation, Minneapolis, Minn.). The MTS machine can apply axial compressive and torsional loads about the longitudinal axis of the spine. This system allows a constant bending moment to be applied uniformly over the length of the spine resulting in a pure sagittal flexion and extension load, with axial load and torsion maintained at zero.

Separate tests were performed for axial compression, torsion, flexion-extension, and lateral bending. Axial load was cycled from 0 to 100 N in compression. Coupled motion in rotation or sagittal bending was allowed. Torsion was cycled from positive to negative 5 N-m with a 50 N compressive preload. Again, coupled motion was allowed by leaving axial load and sagittal bending in load control. Sagittal bending was cycled from flexion to extension with a uniform 2 N-m bending moment with a 5 N tensile preload. Lateral bending was performed from left to right with a uniform 2 N-m bending moment with a 5 N tensile preload. Each test consisted of five sinusoidal load cycles at 0.1 Hz. Specimens were preconditioned over the first four cycles with data from the fifth cycle used for analysis. Data acquisition was continuous throughout each test and stored in a computer data file.

Axial compressive data included axial load (N) and axial displacement (mm). Flexion-extension, torsional, and lateral bending data included axial load (N), torque (N-m), and rotational displacement (degrees). The measurement of axial, flexion-extension, lateral bending and torsional displacement was performed simultaneously using extensometers applied across each of the operated disc levels. Data analysis consisted of stiffness calculation across each disc space for axial load, flexion-extension, torsion, and lateral bending.

Radiographic Analysis: Analysis was carried out on all of the three, six, nine and twelve week radiographic films. The radiographs were analyzed for cage migration and the absence or presence of lucent lines surrounding each cage. If a lucent line was seen on either the AP or lateral radiograph, that cage was noted to possess a lucency.

Histologic Analysis: Following biomechanical testing specimens were removed from the mounting grips and frames. The spines were cut through the mid-axial portion of the C3-, C4, and C6 vertebral bodies thus providing three individual specimens containing the implant in a bone-disc space-bone block. The specimens were then cut into sagittal sections starting on the right lateral side using an Isomet Plus precision saw (Buehler Instruments, Lake Bluff, Ill.). When the sagittal slice revealed the first sign of the cage, two additional 2.5 mm slices were removed. These two slices were then stores in 70 percent alcohol awaiting microradiographic analysis. A third sagittal slice was then removed and set aside for fluorochrome analysis. The remaining specimen is stored in 70 percent alcohol.

The first two slices that contain the cage were then processed for microradiographs. A sagittal microradiograph was obtained in a Hewlett Packard Faxitron unit (Hewlett Packard, McMinnville, Oreg.). Each sagittal microradiograph contained two cage-vertebral body interfaces. Each of these interfaces was graded separately and as to whether or not there was bone or fibrous tissue surrounding the cage. Each interface was then subclassified as to whether or not there was bone growth into the cage from teh respective interface. Thus each disc interspace-cage-end plate junction could be classified as either: (1) cage completely surrounded by bone with bone ingrowth (B—B), (2) cage completely surrounded by bone with fibrous or no ingrowth (B-F/E), (3) cage surrounded by fibrous tissue with fibrous ingrowth (F—F), or (4) cage surrounded by fibrous tissue and empty (F-E).

The presence or absence of a successful arthrodesis was determined from the sagittal microradiographs. If both disc interspace-cage-end plate interfaces were completely surrounded by bone and there was bone consolidation throughout the interspace, then the level was deemed to have a solid arthrodesis. If both interfaces were surrounded by fibrous tissue and the cage was empty, then level was deemed to have a failed arthrodesis. If one interface was surrounded by bone and the other with fibrous tissue, or if both interfaces were surrounded by fibrous tissue and the cage filled with fibrous tissue, then the level was deemed to have an intermediate result.

The third sagittal slice was mounted in polymethylmethacrylate for fluorochrome analysis. Using the Isomet Plus saw, 200 to 360 $\mu$m thick slices were obtained. These slices were then ground to a thickness of 100 $\mu$m using a Maruto ML-512D Speed Lapping machine (Maruto Instruments, Tokyo, Japan). A sagitLal microradiograph was obtained of the specimen at a thickness of 100 $\mu$m to correlate with the fluorochrome analysis. After obtaining this microradiograph the slice was ground down to a thickness of 40 $\mu$m and mounted on a slide for fluorochrome analysis. The presence or absence of each marker around and within the cage allowed us to determine the relative time frame of bone revascularization around and within the cage.

RESULTS: All 21 goats successfully underwent surgery and survived without difficulty during the length of the experiment. No cervical spine wound infection occurred. There were no neurologic complications.

Radiographic Results: None of the cages in any of the groups displaced. In group I there were three cages with lucencies. In group II there were four cages with lucencies. In group III none of the 21 cages exhibited any lucencies.

Microradiograph Results: The results of grading each individual cage-endplate-interface junction are summarized in Table I. The BMP filled cages had a greater number of interfaces surrounded by bone and a greater amount with bone ingrowth than either of the other two groups.

The arthrodesis success rate was greatest for the BMP filled cages at 95% followed by the HA coated (62%) and standard devices (48%). This difference was statistically significant (p=0.002). The unsuccessful arthrodesis rate was 14% for both HA coated and standard groups, and zero for the BMP filled cages. The intermediate results were 38% for the standard cage, 14% for the hydroxyapatite cage, and 5% for the BMP filled cage.

Biomechanical Data: Mean biomechanical stiffness data in axial compression, torsion, flexion, extension, and lateral bending is summarized by group in Table II. There were no statistical differences by group in any of the loading modes tested. While there were no statistically significant differences in stiffness in any loading mode by arthrodesis result, there was a tendency for a cage with a successful arthrodesis to be stiffer than a failed arthrodesis in axial compression, torsion, flexion, and extension.

Fluorochrome Analysis.: There were ten cages in group I that exhibited bone formation completely around the cage. Seven of these cages (70%) exhibited bone revascularization after the three week injection and three (30%) after the six week injection. In group II, thirteen cages exhibited bone formation completely around the cage. Either of these (62%) exhibited revascularization after the three week injection, three (23%) after the six week injection, and two (15%) after the nine week injection. In group III, twenty cages exhibited bone formation completely around the cage. Nineteen of these (95%) exhibited bone revascularization after the three week injection and one (5%) after the six week injection.

Twenty-two of the sixty-three cages in all three groups exhibited bone growth within the cage. In group I, one cage of six (17%) exhibited bone revascularization after the six week injection, and five cages (83%) after the nine week injection. In group II all five cages exhibited bone revascularization after the nine week injection. In group III, three of eleven ages (27%) exhibited bone revascularization after the three week injection, six (55%) after the six week injection, and two (18%) after the nine week injection. Thus, in general, the BMP filled cages exhibited earlier revascularization of bone both around and within the cages compared to the other two groups.

CONCLUSION: The use of an intervertebral fusion cage filled with BMP resulted in a much higher arthrodesis rate and accelerated bone revascularization compared to either autogenous bone filled devices, or autogenous interbody bone grafts with or without plate stabilization.

EXAMPLE 2

Design: Twelve mature female sheep underwent single level midlumbar interbody fusion. All surgical dissections were performed in an identical fashion. Following preparation of the anterior fusion sites the implants were inserted. Sheep were treated with a Threaded Interbody Fusion Device (TIBFD) containing rhBMP-2 carried on a type I fibrillar collagen (Helistat)(n=6) in a single cage, lateral orientation through a retroperitoneal approach. Previous limbs of the study (all n=6) included TIBFD with autogenous bone plugs, autogenous bone plugs alone, or sham (empty) fusion sites. The sheep were allowed to graze immediately post-operatively and no external immobilization was used. All animals were sacrificed six months following surgery. Fourteen additional cadaver sheep spines had been obtained to determine baseline intervertebral mechanical stiffness measures.

Materials: The interbody fusion cages developed and manufactured by Sofamor Danek, Inc., Memphis Tenn. were made of Ti-6A1-4V alloy and designed as closed cylinders. The devices were 14mm in diameter and contained a screw-in end cap to allow for placement of graft materials. The device porosity as described by the manufacturer was 35% overall hole to metal ratio with increased porosity in contact with the intervertebral bodies. The mechanical load to yield is reported to be 80,000 Newtons (maximum human physiologic loads—10,000 Newtons). Cyclic compressive loading from 800 to 9,680 Newtons at 15 Hz over 5,000,000 cycles resulted in no observable microscopic damage or deformation.

The dose of rhBMP-2 was 0.43 mg/ml. The protein in its buffered solution was drip applied to commercial grade type I collagen (Helistat). The composite was then inserted into the cage chamber following which the cage cap was applied. The device was then inserted into the prepared fusion site.

Surgical procedure: A 10 cm rostral to caudal left flank incision was made under sterile conditions. Following incision of the ateral fascia of the external abdominal musculature, the retroperitoneal plane was identified. Proceeding through this plane the intervertebral disc between the L4 and L5 veterbral bodies was cleaned of soft tissue. Segmental vessels were not ligated unless required for additional exposure. The descending aorta was retracted to expose the anterior longitudinal ligament and anterior annulus. A 2 mm guide wire was placed transversely through the intervertebral disc bisecting the disc in the sagittal plane. A cannulated trephine punch was then used over the wire to create a left lateral annulotomy.

A blunt tip "bullet" shaped dilator 7 mm in diameter was used over the same wire to expand the disc space and place the annulus under tension. A four-prong outer sleeve was placed over the distractor and impacted so as to purchase the adjacent vertebral bodies. Side prongs in the disc space aided in maintaining distraction. The dilator was then removed. A bone cutting reamer was placed through the outer sleeve and used to create a transverse hole through the disc space. At least 3 mm of endplate and subchondral bone of the adjacent vertebral bodies were removed during the process. At this point the device was prepared and implanted. Routine closure of external abdominal muscular fascia, subcutaneous tissue and skin was performed.

Mechanical Testing: All sheep that had undergone surgery were mechanically tested for fusion stiffness following sacrifice. In addition, cadaver spines from fourteen untreated sheep were also tested to establish baseline parameters for the L4-L5 motion segment. The L4-L5 intervertebral segments (fusion sites) were tested for stiffness to sagittal and coronal plane bending moments (flexion, extension, right bending, left bending) in all eighteen sheep. For baseline measures, fourteen untreated cadaver sheep spines were also tested for stiffness at the L4-L5 intersegment in the same planes of motion.

Following sacrifice, the spinal columns from L3 to L6 were explanted. Intersegmental ligamentous tissues were retained. The transverse processes were trimmed to facilitate polymethylmethacrylate (PMMA) potting of the L3 and L6 vertebrae. The PMMA pots did not include the L3-L4 or the L5-L6 discs.

Non-destructive mechanical tests were performed with an MTS 812 servohydraulic testing machine. The specimen was mounted in an apparatus such that it was oriented perpendicular to the axis of actuation. One end of the specimen was fixed while the other was free to move and placed directly above the actuator. Pure bending moments were applied using a system of cables and pulleys. Rotational variable differential transformers (RVDT) were attached to the vertebral body via bone screws to measure rotation in the L4-L5 motion segment and to the free end to measure its angle with respect to horizontal. load-displacement data were recorded.

For each test, loads were applied in three cycles consisting of a 5 second ramp per cycle with a maximum applied moment of approximately 10 N-m. Tests were performed in flexion, extension, right bending, and left bending modes sequentially. Stiffness was calculated as the slope of the force versus angular displacement curve at 8 N-m for all groups.

Radiqgraphic Evaluation: Under general anesthesia, anterior-posterior and lateral radiographs were obtained immediately post-operatively, and then two months, four months, and six months following surgery. Measurements of vertebral body heights and disc heights along the lumbar spine were made in the mid-sagittal line using a photo image analyzer (superfine pitch monitor, Image-1/Atsoftware. 1991). All measurements were made on true lateral radiographs. Since measures of the iriterbody disc heights at the fusion sites were obscured by implant materials and "interbody height index" (IB index) was calculated to reflect interbody distraction. This index was calculated as follows: The mid-sagittal span of the fused segments from the cephalad endplate of L4 to the caudal endplate of L5 was measured as the "fusion height". Since the vertebrae were of relatively uniform height, the sum of the mid-sagittal heights of the L3 and L6 vertebrae was used to estimate the some of the heights of the L4 and L5 vertebrae excluding the intervening intervertebral disc. The sum of the L3 and L6 vertebrae was then subtracted from the fusion height to ascertain the "calculated interbody height". In order to correct for differences in magnification this value was expressed as a ratio to average vertebral height and this value was defined as the IB index.

Results: The mechanical testing results from one specimen implanted with TIBFD+rhBMP-2 were excluded due to apparatus errors.

Results of Mechanical Testing Data: Means, standard deviations as a function of group are presented in Table III. Results from overall and pairwise statistical comparisons are presented in Table IV. Mean stiffness was significantly different among the groups (two treatment and unoperated control) for each mode of testing (P=0.005, P=0.0001, P=0.0001, P=0.0001).

All surgically treated intersegments were significantly stiffer than untreated intersegments. That is, sites implanted with TIBFD+rhBMP-2 or TIBFD+autograft compared to those untreated were significantly stiffer to flexion (P=0.0001, P=0.055) extension (P=0.0001, P=0.0001) right bending P=0.0001, P=0.0001) and left bending moments (P=0.0001, P=0.0001). There was no difference in stiffness between intersegments treated with TIBFD+rhBMP-2 and those treated with TIBFD+autograft (comparisons for all modes of testing were P 0.05).

Results of Interbody Heiqht Measures Interbody Height Index: Means standard deviations and results from overall and pairwise statistical comparisons are presented in Table V. There is no differences in the Interbody Height index between TIBFD+rhBMP-2 and TIBFD+autograft at each of the time measures F(4.40)=0.20 P=94). Subsidence occurred primarily in the first two post-operative months in both groups (roughly 20% of the initial interbody disc height) although the decrease in interbody height was not significant (F(2.20)=0.19, P=0.83).

Conclusions: No differences were noted either mechanically or morphologically between the fusions created with TIBFD+rhBMP-2 and those created with TIBFD+autograft. There was a trend toward greater stiffness to flexion with TIBFD+rhBMP-2 but this was not significant. Subsidence tended to occur in both groups in the first two months. Harvesting of autogenous bone graft provides no advantage compared to the use of rhBMP-2 with type I fibrillar collagen in this model.

EXAMPLE 3

Open Porosity Polylactic Acid Polymer (OPLA) is provided in sterile packaged 12.0 mm×6.5 mm×30 mm strips (two strips per package). The pure OPLA is sterilized via gamma irradiation. The rhBMP-2 is provided in freeze-dried powder form and reconstituted intra-operatively in sterile water and supplemented with a buffer vehicle solution. The rhBMP-2 is introduced into the carrier material and the carrier is placed into the hollow interior of a metal fusion cage device. The device is then implanted at the fusion site.

EXAMPLE 4

A rhBMP-2 /collagen implant is prepared from Helistat® Absorbably Collagen Hemostatic Agent (Integra Life-Sciences Corporation) and rhBMP-2. The collagen carrier is placed within the hollow interior of a metal fusion cage device. The device is implanted at the fusion site.

TABLE I

Individual Cage-Interspace-Endplate Bone Ingrowth Results by Cage Goup

| Group | Microradiograph Grade* | | | |
|---|---|---|---|---|
| | B–B | B–F/E | F–F | F–E |
| I | 33% | 29% | 14% | 24% |
| II | 26% | 43% | 12% | 19% |
| III | 53% | 45% | 0% | 2% |

*See text for definition of each grading result.

TABLE II

Biomechanical Stiffness Data by Cage Group

| Group | Axial Compression (N/mm) | Torsion (N-m/degree) | Flexion (N-m/degree) | Extension (N-m/degree) | Lateral Bending (N-m/degree) |
|---|---|---|---|---|---|
| I | 187 (92) | 8.4 (11.7) | 0.99 (0.91) | 5.0 (7.2) | 1.4 (2.2) |
| II | 165 (70) | 10.2 (12.5) | 1.6 (2.7) | 3.4 (2.8) | 2.3 (3.9) |
| III | 313 (388) | 6.7 (10.2) | 0.96 (0.48) | 3.1 (2.4) | 1.0 (0.66) |
| p value | 0.46 | 0.32 | 0.24 | 0.82 | 0.72 |

Values in parenthesis represent standard deviations

TABLE III

Results of Mechanical Testing

| Conditions | n | Flexion Mean ± sd | Extension Mean ± sd | Rt. Bending Mean ± sd | Lt. Bending Mean ± sd |
|---|---|---|---|---|---|
| TIBFD + rhBMP-2 | 5* | 15.91 ± 6.90 | 25.19 ± 10.91 | 19.35 ± 5.82 | 15.40 ± 2.35 |
| TIBFD +autograft | 6 | 11.00 ± 7.81 | 24.55 ± 10.51 | 9.89 ± 4.04 | 19.47 ± 8.56 |
| Untreated | 14 | 6.71 ± 1.40 | 6.03 ± 2.15 | 0.41 ± 0.11 | 4.04 ± 0.90 |
| | 25 | | | | |

TABLE IV

Results of Mechanical Testing

| Compared Conditions | Flexion Mean ± sd. | P | Extension Mean ± sd. | P | Right Bending Mean ± sd. | P | Left Bending Mean ± sd. | P |
|---|---|---|---|---|---|---|---|---|
| TIBFD + rhBMP-2 | 15.91 ± 6.90 | (P = 0.30) | 25.19 ± 10.91 | (P = 0.92) | 19.35 ± 5.82 | (P = 0.36) | 15.40 ± 2.35 | (P = 0.33) |
| TIBFD + autograft | 11.00 ± 7.81 | | 24.55 ± 10.51 | | 15.58 ± 9.89 | | 19.47 ± 8.56 | |
| TIBFD + rhBMP-2 | 15.91 ± 6.90 | (P = 0.0001) | 25.19 ± 10.91 | (P < 0.0001) | 19.35 ± 5.82 | (P < 0.0001) | 15.40 ± 2.35 | (P < 0.0001) |
| Untreated | 6.71 ± 1.40 | | 6.03 ± 2.15 | | 2.98 ± 0.41 | | 4.04 ± 0.90 | |
| TIBFD + autograft | 11.00 ± 7.81 | (P = 0.06) | 24.55 ± 10.51 | (P < 0.0001) | 15.58 ± 9.89 | (P < 0.0001) | 19.47 ± 8.56 | (P < 0.0001) |
| Untreated | 6.71 ± 1.40 | | 6.03 ± 2.15 | | 2.98 ± 0.41 | | 4.04 ± 0.90 | |

TABLE V

| | | Results Interbody Height Index: from 0 to 6 months | | | |
|---|---|---|---|---|---|
| Conditions | n | post op Mean ± sd | 2 months Mean ± sd | 4 months Mean ± sd | 6 months Mean ± sd |
| TIBFD + rhBMP-2 | 6* | 0.20 ± 0.04 | 0.14 ± 0.03 | 0.17 ± 0.04 | 0.15 ± 0.03 |
| TIBFD + autograft | 6 | 0.20 ± 0.03 | 0.15 ± 0.05 | 0.15 ± .05 | 0.16 ± .05 |
| Total measured | 12 | | | | |

What is claimed:

1. A fusion device for facilitating arthrodesis in the disc space between adjacent vertebrae comprising:

a hollow metal body defining a hollow interior with at least one bone ingrowth opening through said body in communication with said hollow interior; and an osteogenic material placed within said hollow interior, said osteogenic material including a bone morphogenic protein in a suitable carrier, wherein said carrier is in the form of at least one sheet, said sheet(s) being foldable to conform to and substantially fill said hollow interior and moldable to extend outward at least partially into said ingrowth opening.

2. A fusion device for facilitating arthrodesis in the disc space between adjacent vertebrae, the vertebrae having facing vertebral endplates, the device comprising:

an elongated rigid body having a length and a first diameter at a first end sized to be greater than the space between the adjacent vertebrae and formed to include an interior chamber, said body having an outer surface with a pair of opposite cylindrical portions and a pair of opposite side walls between said opposite cylindrical portions, said side walls extending along a substantial portion of said length of said body, said body being further formed to define a bone ingrowth opening in each of said opposite cylindrical portions in communication with said interior chamber and with said outer surface;

external threads defined on said pair of opposite cylindrical portions of said outer surface and extending along substantially the entire length of said body; and an osteogenic material disposed within said interior chamber, wherein said osteogenic material includes at least one bone morphogenic protein in a carrier that is in the form of at least one sheet, said sheet(s) being foldable to conform to and substantially fill said interior chamber and moldable to extend outward at least partially into said ingrowth openings.

3. The device of claim 1 wherein the bone morphogenic protein is a recombinant human protein.

4. The device of claim 1 wherein the bone morphogenic protein is rhBMP-2, rhBMP-7 or a mixture thereof.

5. The device of claim 1 wherein the carrier comprises a polylactic acid polymer.

6. The device of claim 1 wherein the hollow metal body is further formed to multiple vascularization openings through said body and in communication with the hollow interior.

7. The device of claim 2 wherein the bone morphogenic protein is a recombinant human protein.

8. The device of claim 2 wherein the bone morphogenic protein is rhBMP-2, rhBMP-7 or a mixture thereof.

9. The device of claim 2 wherein the carrier comprises a polylactic acid polymer.

10. The device of claim 2 wherein at least one of the side walls is formed to include at least one vascularization opening through said side wall and in communication with the interior chamber.

* * * * *